United States Patent
Yoshihara (10) Patent No.: US 9,972,085 B2
(45) Date of Patent: May 15, 2018

(54) ANTINUCLEAR ANTIBODY IMAGE ANALYSIS SYSTEM, ANTINUCLEAR ANTIBODY IMAGE ANALYSIS METHOD, AND ANTINUCLEAR ANTIBODY IMAGE ANALYSIS PROGRAM

(71) Applicant: NEC Corporation, Tokyo (JP)

(72) Inventor: Yoshiko Yoshihara, Tokyo (JP)

(73) Assignee: NEC Corporation, Tokyo (JP)

( * ) Notice: Subject to any disclaimer, the term of this patent is extended or adjusted under 35 U.S.C. 154(b) by 23 days.

(21) Appl. No.: 15/100,898

(22) PCT Filed: Dec. 5, 2014

(86) PCT No.: PCT/JP2014/006085
§ 371 (c)(1),
(2) Date: Jun. 1, 2016

(87) PCT Pub. No.: WO2015/087524
PCT Pub. Date: Jun. 18, 2015

(65) Prior Publication Data
US 2016/0300345 A1 Oct. 13, 2016

(30) Foreign Application Priority Data
Dec. 11, 2013 (JP) .................. 2013-255558

(51) Int. Cl.
*G06K 9/00* (2006.01)
*G06T 7/00* (2017.01)
(Continued)

(52) U.S. Cl.
CPC ....... *G06T 7/0012* (2013.01); *G01N 33/6875* (2013.01); *G06K 9/46* (2013.01);
(Continued)

(58) Field of Classification Search
CPC ........ G06T 7/0012; G06T 2207/30004; G01N 33/6875; G06K 9/46; G06K 9/3233
See application file for complete search history.

(56) References Cited

U.S. PATENT DOCUMENTS

| 7,314,720 B2 * | 1/2008 | De La Paz ........... G01N 33/576 |
| | | 435/287.1 |
| 2006/0204968 A1 * | 9/2006 | Haeupl ................ C12Q 1/6883 |
| | | 435/6.12 |

(Continued)

FOREIGN PATENT DOCUMENTS

| CA | 02702421 A1 | 5/2009 |
| CN | 101874206 A | 10/2010 |

(Continued)

OTHER PUBLICATIONS

Japanese Decision to Grant a Patent issued by the Japan Patent Office for Japanese Application No. 2015-552326 dated Jun. 13, 2017 (5 pages).

(Continued)

*Primary Examiner* — Ali Bayat
(74) *Attorney, Agent, or Firm* — Wilmer Cutler Pickering Hale and Dorr LLP (57) ABSTRACT

Luminance calculation means 81 calculates luminance of a cell nucleus extracted from an antinuclear antibody image of a designated dilution ratio. Titer prediction means 82 predicts an antinuclear antibody titer, using a staining pattern specified from a staining form of the cell nucleus and the luminance at at least one dilution ratio.

8 Claims, 9 Drawing Sheets

(51) Int. Cl.
*G01N 33/68* (2006.01)
*G06K 9/32* (2006.01)
*G06K 9/46* (2006.01)

(52) U.S. Cl.
CPC ....... *G06K 9/00134* (2013.01); *G06K 9/3233* (2013.01); *G06K 9/4652* (2013.01); *G06T 2207/30004* (2013.01)

(56) References Cited

U.S. PATENT DOCUMENTS

| 2008/0016015 | A1 | 1/2008 | Perner | |
| 2010/0267168 | A1* | 10/2010 | Hiemann | G01N 33/564 436/518 |
| 2012/0308996 | A1* | 12/2012 | Knutter | G01N 33/554 435/5 |

FOREIGN PATENT DOCUMENTS

| CN | 102667483 A | 9/2012 |
| EP | 2362222 A1 | 8/2011 |
| JP | H08-304284 A | 11/1996 |
| JP | H09-218202 A | 8/1997 |
| JP | 2010-210290 A | 9/2010 |
| JP | 2011-503586 A | 1/2011 |
| JP | 2011-043350 A | 3/2011 |
| JP | 2011-075278 A | 4/2011 |
| JP | 2013-520664 A | 6/2013 |
| WO | WO-2000-054056 A1 | 9/2000 |
| WO | WO-2011/101487 A1 | 8/2011 |

OTHER PUBLICATIONS

Bossuyt, X., et al., "Detection of antinuclear antibodies by automated indirect immunofluorescence analysis," Clinica Chimica Acta, vol. 415, pp. 101-106 (2013).

Chinese Office Action issued by the State Intellectual Property Office of People's Republic of China for Chinese Application No. 201480066893.8 dated Mar. 20, 2017 (16 pages).

International Search Report corresponding to PCT/JP2014/006085 dated Mar. 10, 2015 (5 pages).

Tetsuo Nakabayashi et al., "Simplification of antinuclear antibody determination by flourescent image analysis equipment 'Image titer'", The Journal of Clinical Laboratory Instruments and Reagents, 1999, vol. 22, No. 1, pp. 69 to 72 (7 pages).

Kazuto Nakamura, Kunimitsu Machidda, Fumihiko Ban, Isamu Seto, "Image Titer Workstation (Keiko Gazo Kaiseki Sochi) Mochiita Kokakukotai Sokutei no Kisoteki Kento", Japanese Journal of Clinical Laboratory Automation, Aug. 1, 2000 (Aug. 1, 2000), vol. 25, No. 4, p. 412.

* cited by examiner

|   | 1-Sp | 2-Sp | 3-Sp | 4-Sp |
|---|---|---|---|---|
| 1 | 187.3502 | 63.77375 | 161.9601 | 178.739 |
| 2 | 177.9046 | 34.93392 | 123.5702 | 126.2197 |
| 3 | 141.5657 | 26.80955 | 76.09472 | 91.02653 |
| 4 | 104.298 | 14.5395 | 37.56092 | 49.34534 |
| 5 | 42.7482 |  | 19.88096 | 22.3063 |
| 6 | 25.68736 |  | 11.54458 | 13.67692 |
| 7 | 13.95989 |  | 7.390246 | 8.836105 |
| 8 | 9.226042 |  |  |  |

(a)

|   | 1-Ho | 2-Ho | 3-Ho | 4-Ho |
|---|---|---|---|---|
| 1 | 27.21397 | 177.4415 | 203.0683 | 75.30833 |
| 2 | 15.02625 | 139.1358 | 181.5184 | 54.6809 |
| 3 | 9.996191 | 83.1296 | 119.8619 | 28.78245 |
| 4 |  | 43.46571 | 81.09642 | 16.92302 |
| 5 |  | 28.94107 | 54.63451 | 9.595591 |
| 6 |  | 17.5446 | 29.83421 |  |
| 7 |  | 9.713809 | 16.85999 |  |
| 8 |  |  | 10.75865 |  |

(b)

|   | 1-Nu | 2-Nu | 3-Nu | 4-Nu |
|---|---|---|---|---|
| 1 | 197.0749 | 27.50953 | 186.5971 | 73.84794 |
| 2 | 168.2976 | 12.92352 | 139.8777 | 32.98942 |
| 3 | 89.96015 |  | 100.8251 | 13.38331 |
| 4 | 61.75278 |  | 55.17062 | 11.90589 |
| 5 | 24.27887 |  | 31.62067 |  |
| 6 | 14.87486 |  | 21.3783 |  |
| 7 |  |  | 12.81249 |  |
| 8 |  |  |  |  |

(c)

|   | 1-Dis | 2-Dis | 3-Dis | 4-Dis |
|---|---|---|---|---|
| 1 | 60.9997 | 34.49387 | 119.6293 | 21.92244 |
| 2 | 43.53478 | 33.73292 | 106.1738 | 19.14149 |
| 3 | 40.98694 | 25.6784 | 82.05997 | 15.25245 |
| 4 | 25.29147 | 18.52692 | 68.94591 |  |
| 5 | 26.73341 | 1 | 35.98857 |  |
| 6 | 16.7359 |  | 26.91667 |  |
| 7 | 14.01007 |  | 18.75155 |  |
| 8 | 8.676878 |  | 15.44948 |  |

ANTINUCLEAR ANTIBODY IMAGE ANALYSIS SYSTEM, ANTINUCLEAR ANTIBODY IMAGE ANALYSIS METHOD, AND ANTINUCLEAR ANTIBODY IMAGE ANALYSIS PROGRAM

CROSS-REFERENCE TO RELATED APPLICATIONS

This application is a national stage application of International Application No. PCT/JP2014/006085 entitled "Antinuclear Antibody Image Analysis System, Antinuclear Antibody Image Analysis Method, and Antinuclear Antibody Image Analysis Program" filed on Dec. 5, 2014, which claims priority to Japanese Application No. 2013-255558 filed on Dec. 11, 2013, the disclosures of which are hereby incorporated by reference in their entirety.

TECHNICAL FIELD

The present invention relates to an antinuclear antibody image analysis system, antinuclear antibody image analysis method, and antinuclear antibody image analysis program for analyzing an antinuclear antibody image to predict a titer.

BACKGROUND ART

Antinuclear antibody detection is used in important tests for the diagnosis, treatment policy decision, prognosis estimation, etc. of connective tissue disease which is an autoimmune disease. The most useful method for autoantibody screening is the immunofluorescence. In this method, a patient's serum diluted to a predetermined concentration is added to human laryngeal cancer-derived epithelial cells called HEp-2 cells cultured on glass slides to cause a reaction, and then whether or not an antibody reacting with an autoantigen in the cells is present is detected using a fluorochrome-labeled secondary antibody.

A fluorescence pattern and an antibody titer (titer) are obtained as antinuclear antibody test results by the immunofluorescence. There are six main fluorescence patterns, namely, speckled pattern, homogeneous pattern, peripheral pattern, discrete speckled pattern, nucleolar pattern, and cytoplasmic pattern. The determined titer is expressed as 40-fold positive, 80-fold positive, 160-fold positive, or the like. 40-fold positive means that the fluorescence pattern is recognizable in the case of diluting the patient serum 40-fold but is not recognizable in the case of diluting the patient serum at a higher ratio (e.g. 80-fold).

The determination of an antinuclear antibody by the immunofluorescence is performed in the following two steps. In the first step, samples with a given dilution ratio (e.g. 40-fold) are subjected to a qualitative test. The qualitative test typically involves positive/negative determination visually made through microscopic observation. Samples determined as negative by microscopic examination under the fluorescence microscope are regarded as antinuclear antibody negative.

In the second step which follows, samples determined as positive in the qualitative test are further processed. Once determined as antinuclear antibody positive in the qualitative test, glass slides with the serum being doubling-diluted are prepared and a quantitative test for the antibody titer based on the dilution ratio is conducted. Here, the maximum dilution ratio giving a positive result is set as the antibody titer. The fluorescence pattern of each sample is also determined.

Patent Literature (PTL) 1 describes a method of final antibody titer measurement in the measurement of antibodies against nuclear and cytoplasmic antigens in human serum by means of indirect immunofluorescence assay. In the measurement method described in PTL 1, the final antibody titer of the patient serum is calculated based on the initial antibody titer of the patient serum and the exposure time and maximum effective exposure time (final exposure time) of the camera.

CITATION LIST

Patent Literature

PTL 1: Japanese Translation of PCT International Application Publication No. 2011-503586

SUMMARY OF INVENTION

Technical Problem

The typical test evaluation involves positive/negative determination visually made through microscopic observation as mentioned above, which is problematic in terms of reproducibility and objectivity. In the case of evaluation using a system for displaying a stained sample image on a display, too, positive/negative determination is visually made, which is problematic in terms of reproducibility and objectivity.

There is also a problem in that, in the case where the qualitative test results in antinuclear antibody positive, glass slides with the serum being doubling-diluted need to be prepared for the quantitative test, and up to which dilution ratio the reaction is seen needs to be checked for each glass slide to determine the titer. The same applies in the case of using antinuclear antibody images.

PTL 1 describes a formula for calculating the final antibody titer of the patient serum using the initial antibody titer of the patient serum and the exposure time and final exposure time of the camera. The use of the calculation formula described in PTL 1 enables determination of a certain titer. However, the measurement method described in PTL 1 has a problem in that the accuracy of the calculated antibody titer is low because the formula for calculating the antibody titer is defined by a simple linear equation. Thus, the use of the measurement method described in PTL 1 can reduce the operating cost but has a problem of being unable to enhance titer prediction accuracy.

The present invention accordingly has an object of providing an antinuclear antibody image analysis system, antinuclear antibody image analysis method, and antinuclear antibody image analysis program that can reduce the operating cost in predicting a titer using an antinuclear antibody image while maintaining titer prediction accuracy.

Solution to Problem

An antinuclear antibody image analysis system according to the present invention includes: luminance calculation means which calculates luminance of a cell nucleus extracted from an antinuclear antibody image of a designated dilution ratio; and titer prediction means which predicts an antinuclear antibody titer, using a staining pattern specified from a staining form of the cell nucleus and the luminance at at least one dilution ratio.

An antinuclear antibody image analysis method according to the present invention includes: calculating luminance of a cell nucleus extracted from an antinuclear antibody image of a designated dilution ratio; and predicting an antinuclear antibody titer, using a staining pattern specified from a staining form of the cell nucleus and the luminance at at least one dilution ratio.

An antinuclear antibody image analysis program according to the present invention causes a computer to execute: a luminance calculation process of calculating luminance of a cell nucleus extracted from an antinuclear antibody image of a designated dilution ratio; and a titer prediction process of predicting an antinuclear antibody titer, using a staining pattern specified from a staining form of the cell nucleus and the luminance at at least one dilution ratio.

Advantageous Effects of Invention

According to the present invention, the operating cost in predicting a titer using an antinuclear antibody image can be reduced while maintaining titer prediction accuracy.

DESCRIPTION OF EMBODIMENT

The following describes an exemplary embodiment of the present invention with reference to drawings.

Figure 1:
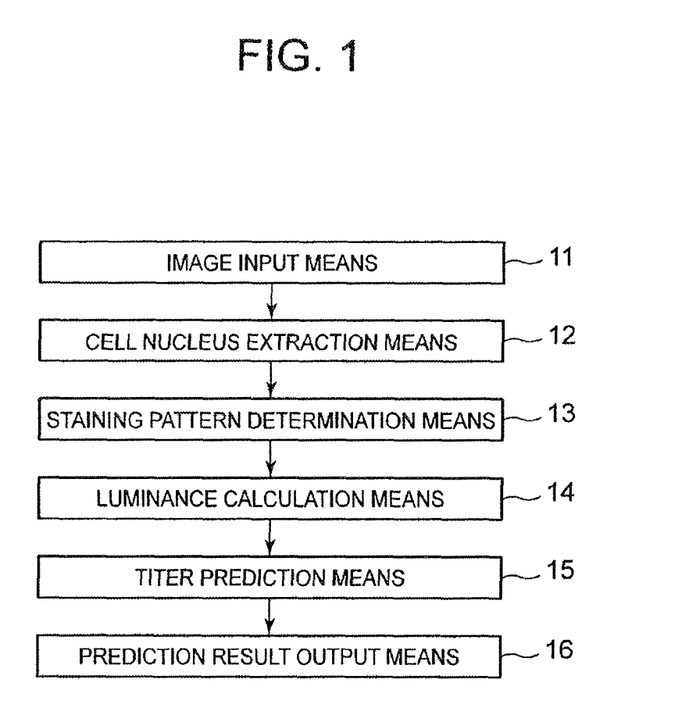
FIG. 1 is a block diagram depicting an exemplary embodiment of an antinuclear antibody image analysis system according to the present invention.

FIG. 1 is a block diagram depicting an exemplary embodiment of an antinuclear antibody image analysis system according to the present invention. The antinuclear antibody image analysis system in this exemplary embodiment includes image input means 11, cell nucleus extraction means 12, staining pattern determination means 13, luminance calculation means 14, titer prediction means 15, and prediction result output means 16.

The image input means 11 receives an input antinuclear antibody image. The input antinuclear antibody image is an image of an antinuclear antibody diluted at a specific ratio. The input antinuclear antibody image may have any ratio, such as 40-fold dilution, 80-fold dilution, or 160-fold dilution, as long as it is a specified ratio. In this exemplary embodiment, an image obtained by capturing a secondary antibody labeled according to the immunofluorescence is used as an antinuclear antibody image. The input antinuclear antibody image is, however, not limited to an image generated using the immunofluorescence.

The image input means 11 may read an antinuclear antibody image from storage means (not depicted) for storing images, or receive an image transmitted from another device via a communication network (not depicted).

The cell nucleus extraction means 12 extracts each cell nucleus from the input antinuclear antibody image. Here, the cell nucleus extraction means 12 may extract each of an interphase cell nucleus and a mitotic phase cell nucleus from the antinuclear antibody image, based on the luminance, shape, etc. of the cell nucleus. By extracting the mitotic phase cell nucleus, the below-mentioned staining pattern can be specified with higher accuracy. Any method may be used to extract the cell nucleus from the antinuclear antibody image, and the cell nucleus extraction means 12 may extract the cell nucleus from the antinuclear antibody image using a widely known method.

The staining pattern determination means 13 determines an antinuclear antibody pattern from the extracted cell nucleus. For example, the immunofluorescence using a fluorochrome mainly classifies antinuclear antibodies into speckled pattern, homogeneous pattern, peripheral pattern, discrete speckled pattern, nucleolar pattern, and cytoplasmic pattern depending on the staining form. The staining pattern determination means 13 accordingly determines which of these patterns the antinuclear antibody can be classified as, based on the staining form of the extracted cell nucleus. Given that the antinuclear antibody pattern is specified based on the staining form of the cell nucleus, the pattern is hereafter referred to as a staining pattern.

For example, in the case where the entire cell nucleus is stained homogeneously, the staining pattern determination means 13 may determine the antinuclear antibody as homogeneous staining pattern. The staining pattern determination means 13 may determine the staining pattern of the antinuclear antibody using any other widely known method.

Some cell nuclei show a feature of a plurality of staining forms. In such a case, the antinuclear antibody cannot be limited to one staining pattern. The staining pattern determination means 13 may accordingly determine that the target antinuclear antibody possibly has a plurality of staining patterns. Thus, the staining pattern determination means 13 may specify not only one staining pattern but also a plurality of staining patterns from the staining form of the cell nucleus.

The luminance calculation means 14 calculates the luminance of the staining region of the cell nucleus. An example of the luminance calculation method is described below. After the cell nucleus extraction means 12 extracts the interphase cell nucleus and the mitotic phase cell nucleus, the luminance calculation means 14 selects the interphase cell nucleus from the extracted cell nuclei.

Typically, a fluorochrome that develops green color is used to stain cell nuclei. The luminance calculation means 14 accordingly calculates the average green value out of RGB, for each selected interphase cell nucleus. As many average green values as cell nuclei are obtained as a result.

The luminance calculation means 14 then calculates the average green value of the cell nuclei, in order to calculate one luminance value for the whole image. In other words, the luminance can be calculated by the following Formula 1.

Luminance=(sum of average green values of cell nuclei)/(number of cell nuclei)   (Formula 1).

Through the use of Formula 1, one luminance value is calculated for each image. Thus, the luminance calculation means 14 may calculate the average value of the predetermined green value from each cell nucleus, and set, as the luminance, the average green value of the whole image calculated using the calculated average value of each cell nucleus. The luminance calculation method is, however, not limited to the calculation method using Formula 1.

The titer prediction means 15 predicts the titer of the antinuclear antibody shown in the image, using the specified staining pattern and the calculated luminance of cell nuclei. Here, the titer prediction means 15 predicts the titer using the luminance calculated for the antinuclear antibody image of one specific dilution ratio. Hence, the antinuclear antibody image input to the image input means 11 may be only an image of a specific dilution ratio for one antinuclear antibody.

The titer prediction means 15 in this exemplary embodiment predicts, based on the luminance calculated from the antinuclear antibody image of the specific dilution ratio, the luminance of an antinuclear antibody image of one or more other dilution ratios depending on the properties of each staining pattern. In detail, the titer prediction means 15 calculates a function indicating the relationship between the dilution ratio and the luminance, for each staining pattern. Typically, the luminance is lower when the dilution ratio is higher, and so the function represented by the dilution ratio and the luminance is a monotonically decreasing function. Given that the function is used to predict the titer, the curve represented by the function is hereafter also referred to as a titer prediction curve. The titer prediction curve is therefore a curve indicating the relationship between the dilution ratio and the luminance.

The titer prediction means 15 specifies, based on the calculated function, a dilution ratio at which the luminance is below a predetermined threshold, and determines the titer from the specified dilution ratio. The threshold is used for determining whether or not the staining pattern is visually identifiable, and is preset for each staining pattern according to technicians' empirical rules and the like.

The method of specifying the function is described in detail below. Let x be a variable denoting the dilution ratio, and y be a variable denoting the luminance. Then, the titer prediction curve is expressed by the following Formula 2. The variable x denoting the dilution ratio is a variable having the following relationship with a dilution ratio x':

$x = \log_2 x' - C$ (where $C$ is a constant).

$\log_2 y = ax + \log_2 b'$ (Formula 2).

Modifying Formula 2 yields the following Formula 3.

$y = b' \cdot 2^{ax}$ (Formula 3).

In Formulas 2 and 3, a is a constant defined for each staining pattern and is predetermined according to empirical rules and the like, and b' is a value determined depending on the calculated luminance.

The luminance calculation means 14 calculates, for a given dilution ratio $x_1'$, a variable $x_1 (= \log_2 x_1' - C)$ denoting the dilution ratio and cell nucleus luminance $y_1$. Then, the titer prediction means 15 assigns the variable $x_1$ denoting the dilution ratio and the luminance $y_1$ to x and y in Formula 2 or 3, to yield b'. Since a is a predetermined constant, once b' is obtained, the curve is uniquely specified. The titer prediction means 15 then specifies a dilution ratio $y_2$ at which the luminance is below a threshold t set for the specified staining pattern. The titer prediction means 15 may predict, as the titer, the maximum dilution ratio from among all dilution ratios that are lower than the dilution ratio $y_2$ and are used to determine the titer.

Figure 2:
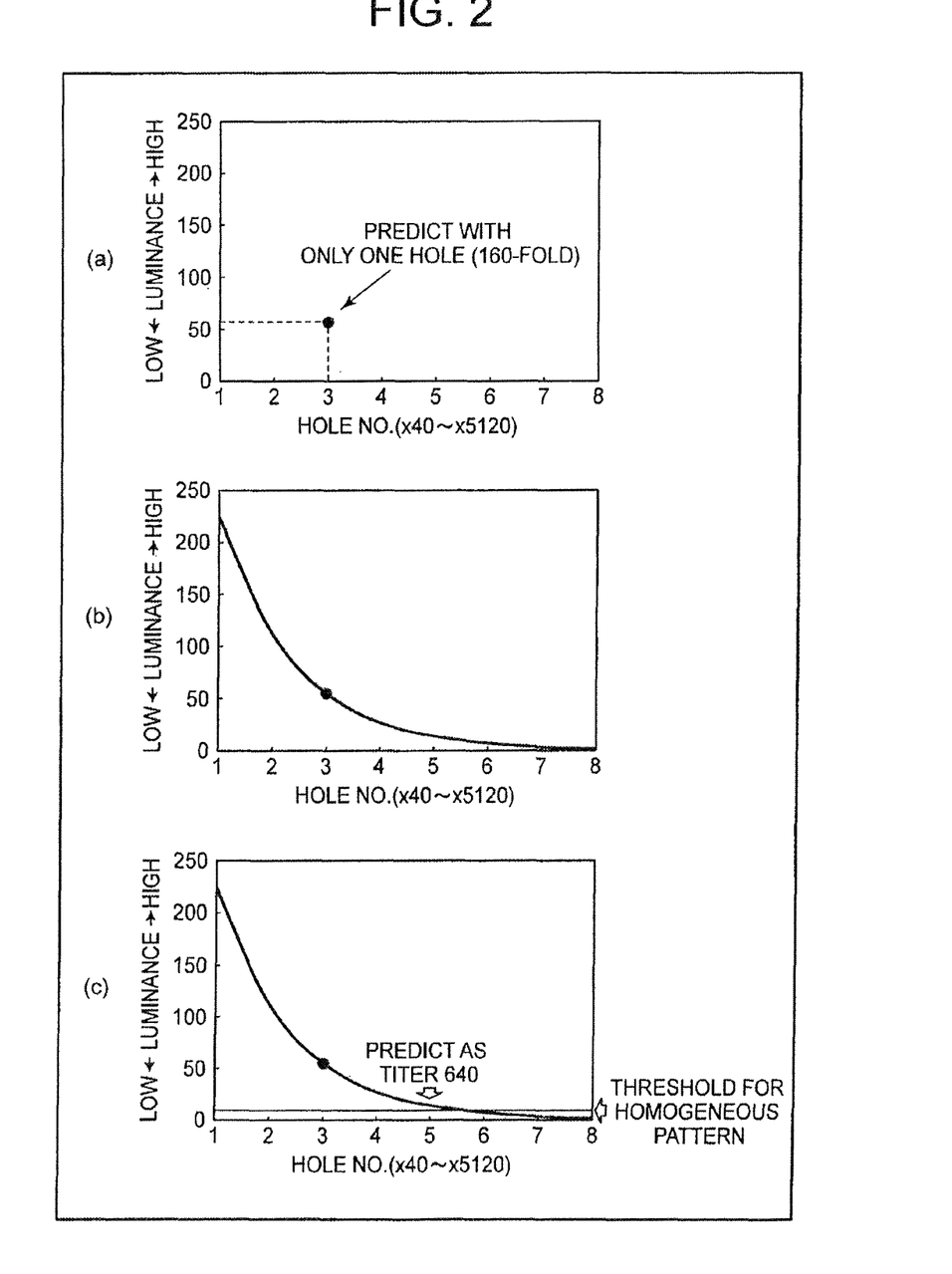
FIG. 2 is an explanatory diagram depicting an example of the titer prediction method.

FIG. 2 is an explanatory diagram depicting an example of the titer prediction method. FIG. 2 depicts an example where the staining pattern determination means 13 determines the staining pattern as homogeneous pattern. In the graph in FIG. 2, the horizontal axis represents the variable denoting the dilution ratio, and the vertical axis represents the luminance. The dilution ratio in the horizontal axis is expressed by a hole No. (the variable denoting the dilution ratio), where the dilution ratios of 40-fold, 80-fold, 160-fold, 320-fold, 640-fold, 1280-fold, 2560-fold, and 5120-fold are respectively assigned to Nos. 1 to 8.

In the example depicted in FIG. 2, No. 3 (160-fold) is selected as the dilution ratio subjected to luminance calculation (see FIG. 2(a)). Substituting the selected dilution ratio and the luminance at the dilution ratio into Formula 2 or 3 yields b'. Since a is predetermined for homogeneous pattern which is the staining pattern, the titer prediction curve is calculated as depicted in FIG. 2(b).

A threshold is predetermined for homogeneous pattern which is the staining pattern. In the example depicted in FIG. 2(c), the dilution ratio at which the titer prediction curve is below the threshold is between Nos. 5 and 6. Hence, the titer prediction means 15 predicts, as the titer, No. 5 (640-fold) which is the maximum dilution ratio from among the dilution ratios subjected to determination as the titer.

Although the dilution ratio No. 3 (160-fold) is selected in the example depicted in FIG. 2, the selected ratio is not limited to No. 3 (160-fold), and may be any dilution ratio. The titer prediction means 15 in this exemplary embodiment calculates the titer prediction curve of the range covering both before and after the dilution ratio. Therefore, for example in the case where the dilution ratio No. 3 is selected, not only the luminance at the dilution ratio from No. 4 and succeeding numbers but also the luminance at the dilution ratio from No. 2 and preceding numbers can be equally predicted.

Thus, the titer prediction means 15 calculates the titer prediction curve from the specified staining pattern and the luminance at the specific dilution ratio, and specifies the dilution ratio at which the luminance is below the threshold. Since there is no need to calculate the luminance at the plurality of dilution ratios, the titer calculation cost can be reduced.

Typically, diluted serum is gradually diluted to determine the titer, and so there is a need to prepare serum at a plurality of dilution ratios and make positive/negative determination for the serum of each dilution ratio, as mentioned earlier. In this exemplary embodiment, on the other hand, only serum at a specific dilution ratio needs to be prepared and imaged, with there being no need to prepare serum at other dilution ratios. This saves the cost of preparing glass slides by doubling-diluting the serum, and also saves the time and effort in observing each doubling-diluted serum.

Moreover, in this exemplary embodiment, the titer prediction curve is expressed as the relationship indicating exponential decay, and the function is defined according to the constant a set for each staining pattern. The use of such a titer prediction curve allows the relationship between the dilution ratio and the luminance to be expressed more appropriately, and as a result enhances the titer prediction accuracy.

In the case where the staining pattern determination means 13 determines that the target antinuclear antibody possibly has a plurality of staining patterns, the titer prediction means 15 may calculate the titer prediction curve to predict the titer for each of the possible staining patterns.

In this exemplary embodiment, the dilution ratio of the serum used in the quantitative test is any dilution ratio. Therefore, dilution ratios (e.g. 10-fold, 100-fold, etc.) other than the above-mentioned 40-fold, 80-fold, 160-fold, and the like are equally applicable.

Although the above describes the method of predicting the titer using the antinuclear antibody image of one specific dilution ratio, the number of dilution ratios used is not limited to 1. The use of antinuclear antibody images of a plurality of dilution ratios contributes to higher titer prediction accuracy.

The prediction result output means 16 outputs the prediction result by the titer prediction means 15. Any method may be used to output the prediction result. For example, the prediction result output means 16 may output only the titer of the input antinuclear antibody image. Alternatively, the prediction result output means 16 may display the function calculated by the titer prediction means 15 and the threshold in graph form. The prediction result output means 16 is realized by, for example, a display device and the like.

The cell nucleus extraction means 12, the staining pattern determination means 13, the luminance calculation means 14, and the titer prediction means 15 are realized by a CPU of a computer operating according to a program (antinuclear antibody image analysis program). For example, the program may be stored in a storage unit (not depicted) in the antinuclear antibody image analysis system, with the CPU reading the program and, according to the program, operating as the cell nucleus extraction means 12, the staining pattern determination means 13, the luminance calculation means 14, and the titer prediction means 15.

Alternatively, the cell nucleus extraction means 12, the staining pattern determination means 13, the luminance calculation means 14, and the titer prediction means 15 may each be realized by dedicated hardware.

Figure 3:
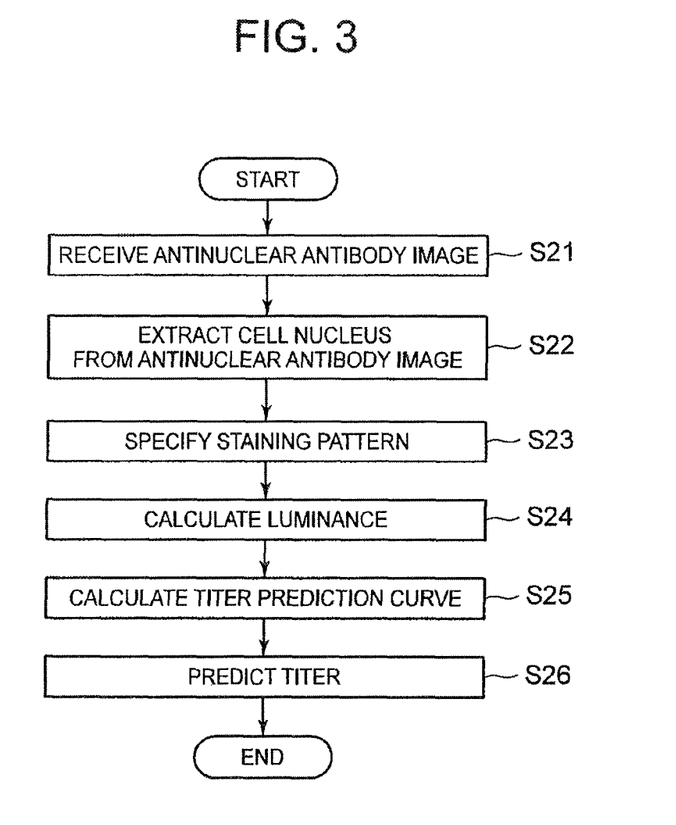
FIG. 3 is a flowchart depicting an example of the operation of the antinuclear antibody image analysis system.

The operation of the antinuclear antibody image analysis system in this exemplary embodiment is described below. FIG. 3 is a flowchart depicting an example of the operation of the antinuclear antibody image analysis system in this exemplary embodiment.

When the image input means 11 receives the antinuclear antibody image (step S21), the cell nucleus extraction means 12 extracts the cell nucleus from the antinuclear antibody image (step S22). The staining pattern determination means 13 specifies the staining pattern of the antinuclear antibody based on the staining form of the extracted cell nucleus (step S23). The luminance calculation means 14 calculates the luminance of the extracted cell nucleus (step S24).

The titer prediction means 15 calculates the titer prediction curve based on the specified staining pattern and the calculated luminance at the specific dilution ratio (step S25). The titer prediction means 15 then determines the dilution ratio at which the luminance is below the threshold from the titer prediction curve, to predict the titer (step S26).

As described above, according to this exemplary embodiment, the luminance calculation means 14 calculates the luminance in the staining region of the cell nucleus extracted from the antinuclear antibody image of the designated dilution ratio, and the titer prediction means 15 predicts the titer of the antinuclear antibody using the specified staining pattern and the luminance at the designated dilution ratio. In this way, the operating cost in predicting the titer using the antinuclear antibody image can be reduced while maintaining titer prediction accuracy.

In detail, according to this exemplary embodiment, not only the cost of preparing glass slides by doubling-diluting the serum but also the time and effort in observing each of the doubling-diluted glass slides can be saved. In other words, determination can be performed at one time for the number of holes made in the glass slide.

EXAMPLE

The following describes the present invention by way of specific examples, although the scope of the present invention is not limited to the following examples. The following description concerns four main staining patterns, namely, speckled pattern, homogeneous pattern, nucleolar pattern, and discrete speckled pattern.

First, glass slides were prepared by doubling-diluting serum for four cases for which each staining pattern was specified, and images of stained samples of different dilution ratios were obtained. In this example, serum with the titer of 40-fold was doubling-diluted up to the titer of 5120-fold at the maximum, and an image of each titer was obtained.

Next, each cell nucleus was extracted from the obtained image, and the luminance was calculated. In this example, the average luminance value calculated from the image was used as the luminance. The luminance depicted in FIG. 4 was obtained as a result. The luminance calculated from the image is hereafter also referred to as a measurement value.

Figure 4:
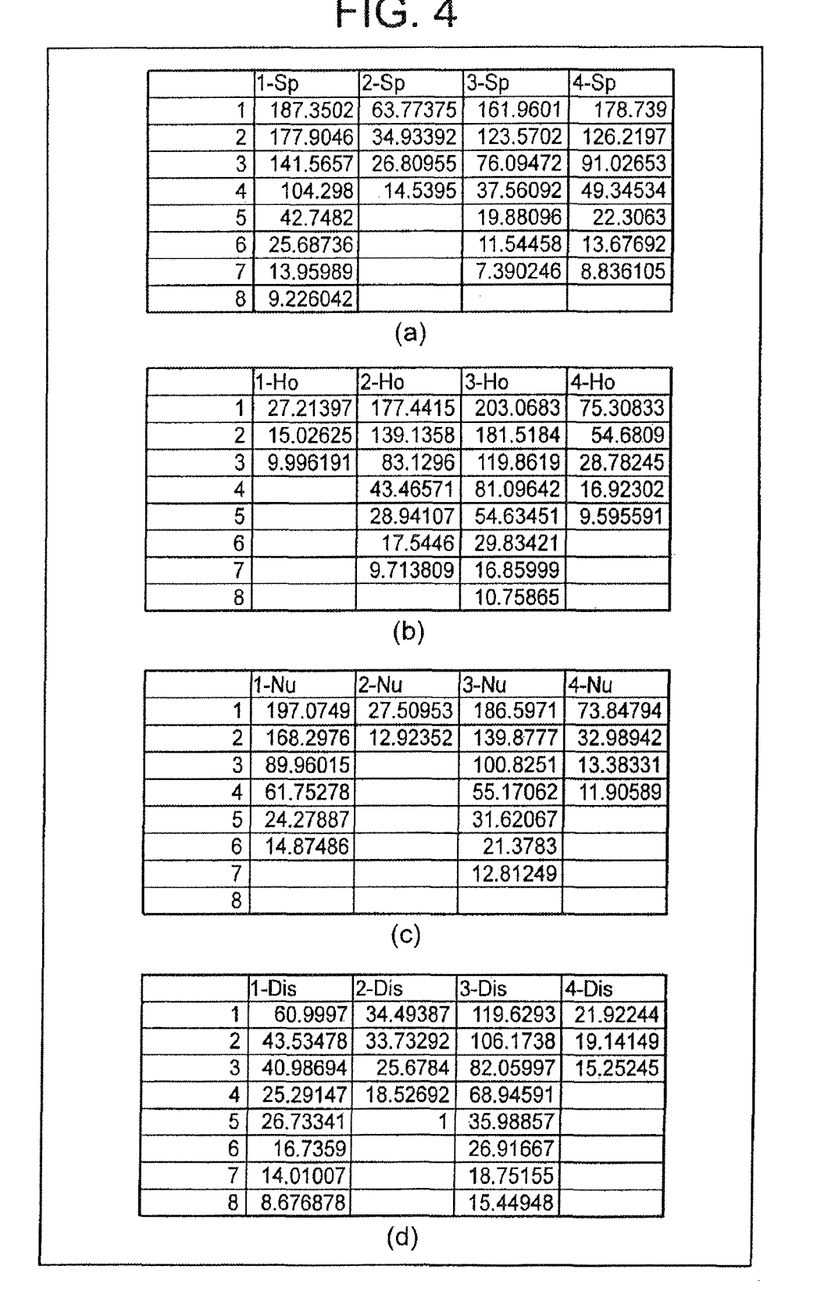
FIG. 4 is an explanatory diagram depicting luminance at each titer.

FIG. 4 is an explanatory diagram depicting the luminance at each titer. The values in FIGS. 4(a), (b), (c), and (d) are respectively the luminance values calculated from the images of the staining patterns, i.e. speckled pattern, homogeneous pattern, nucleolar pattern, and discrete speckled pattern.

The luminance at the titer of 160-fold was then substituted into the above-mentioned Formula 2 or 3 to calculate the constant b', thus calculating the titer prediction curve. Here, the constant a in Formula 2 or 3 is a value predetermined for each staining pattern.

Figure 5:
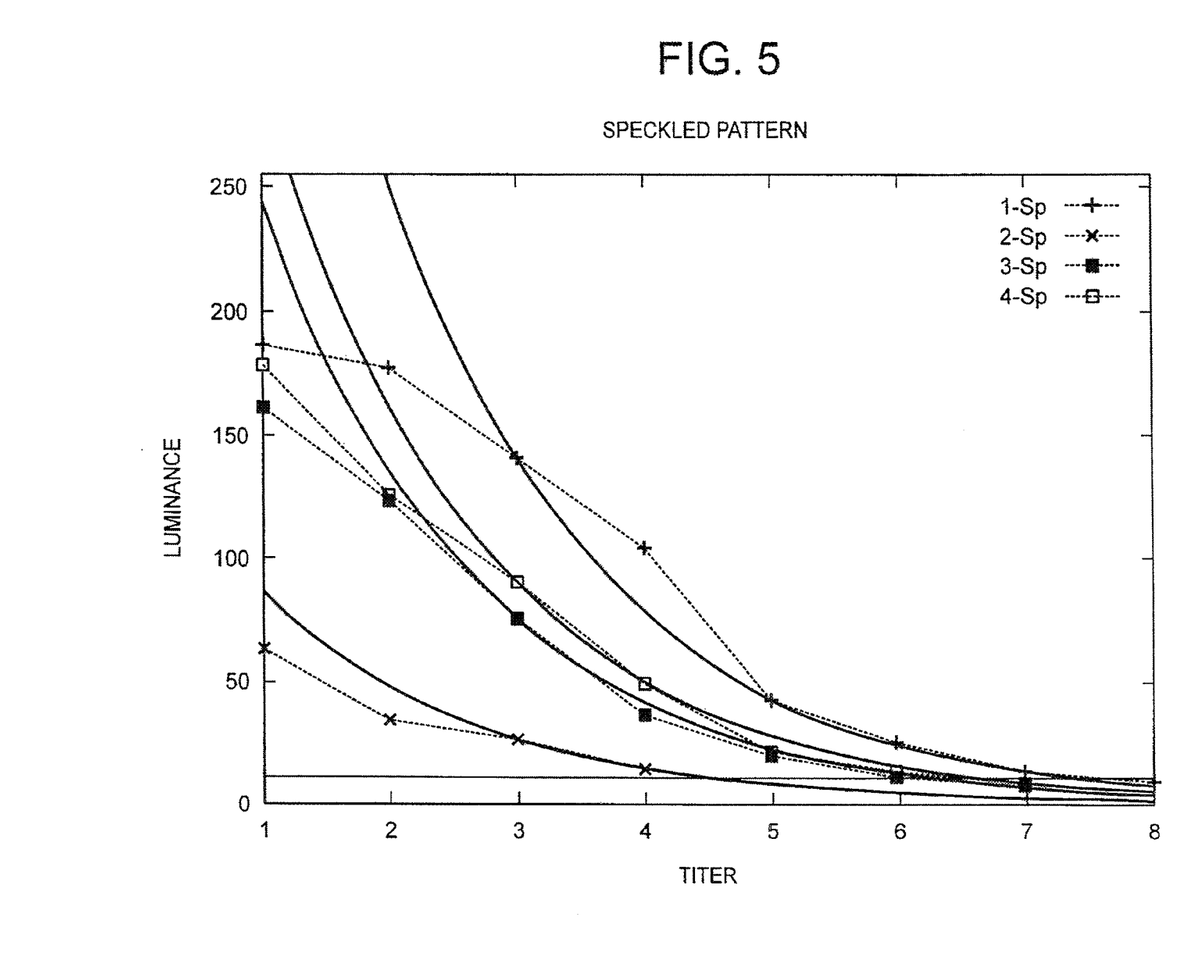
FIG. 5 is an explanatory diagram depicting the relationship between the titer and the luminance in speckled pattern.
Figure 6:
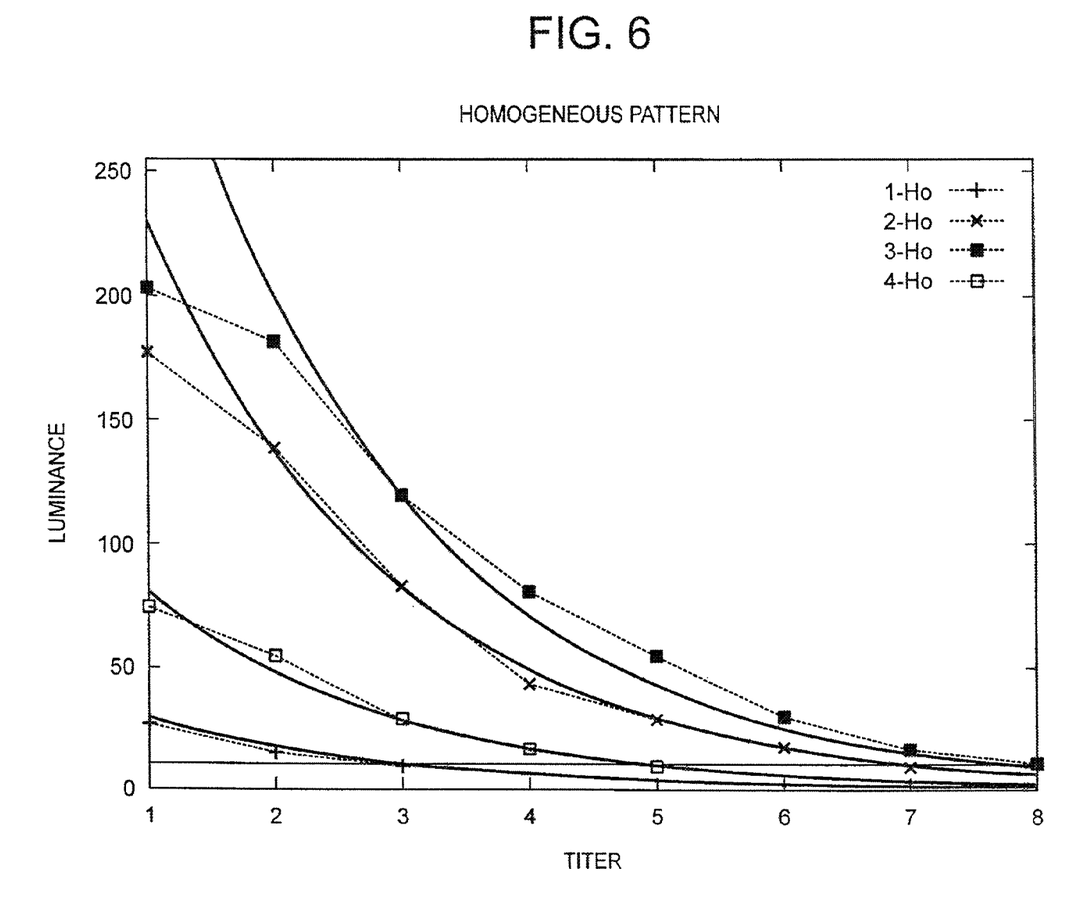
FIG. 6 is an explanatory diagram depicting the relationship between the titer and the luminance in homogeneous pattern.
Figure 7:
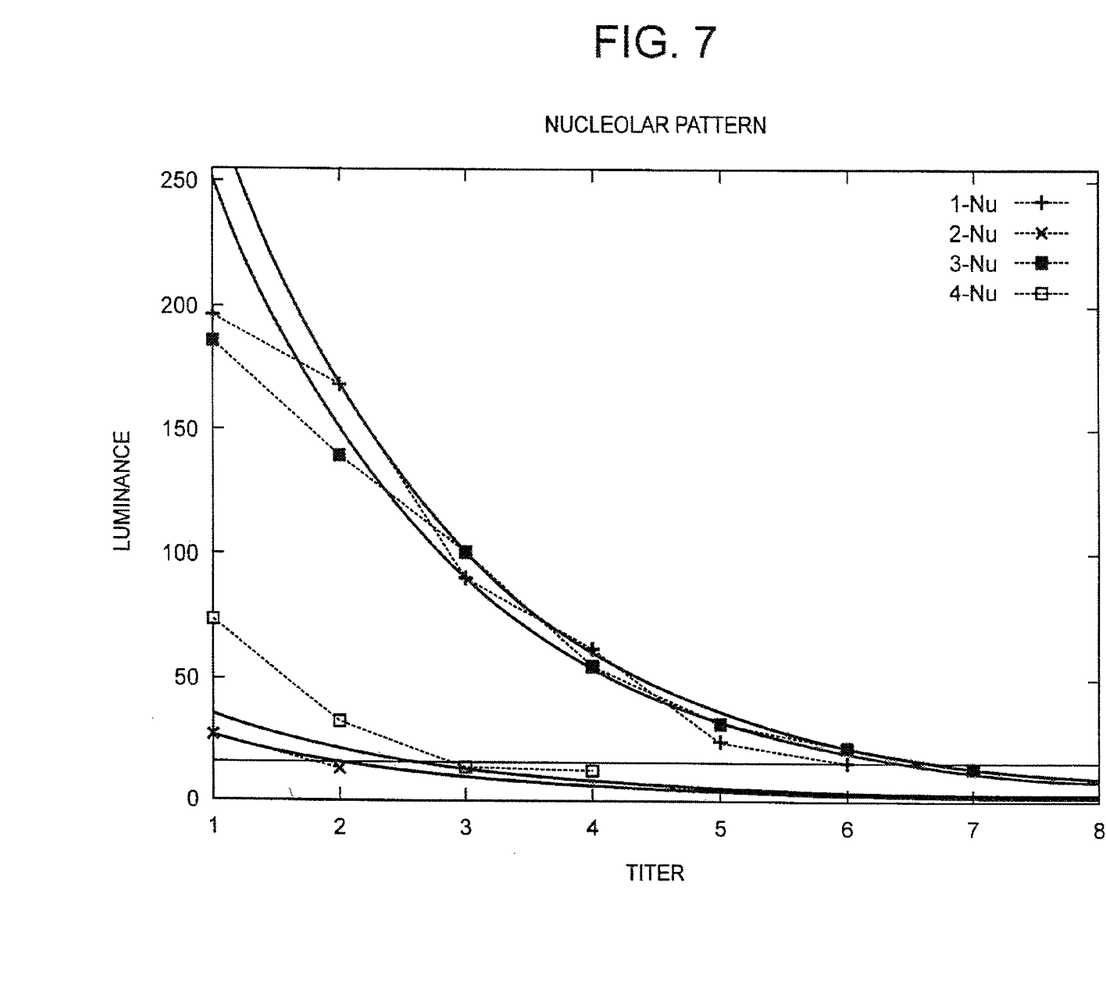
FIG. 7 is an explanatory diagram depicting the relationship between the titer and the luminance in nucleolar pattern.
Figure 8:
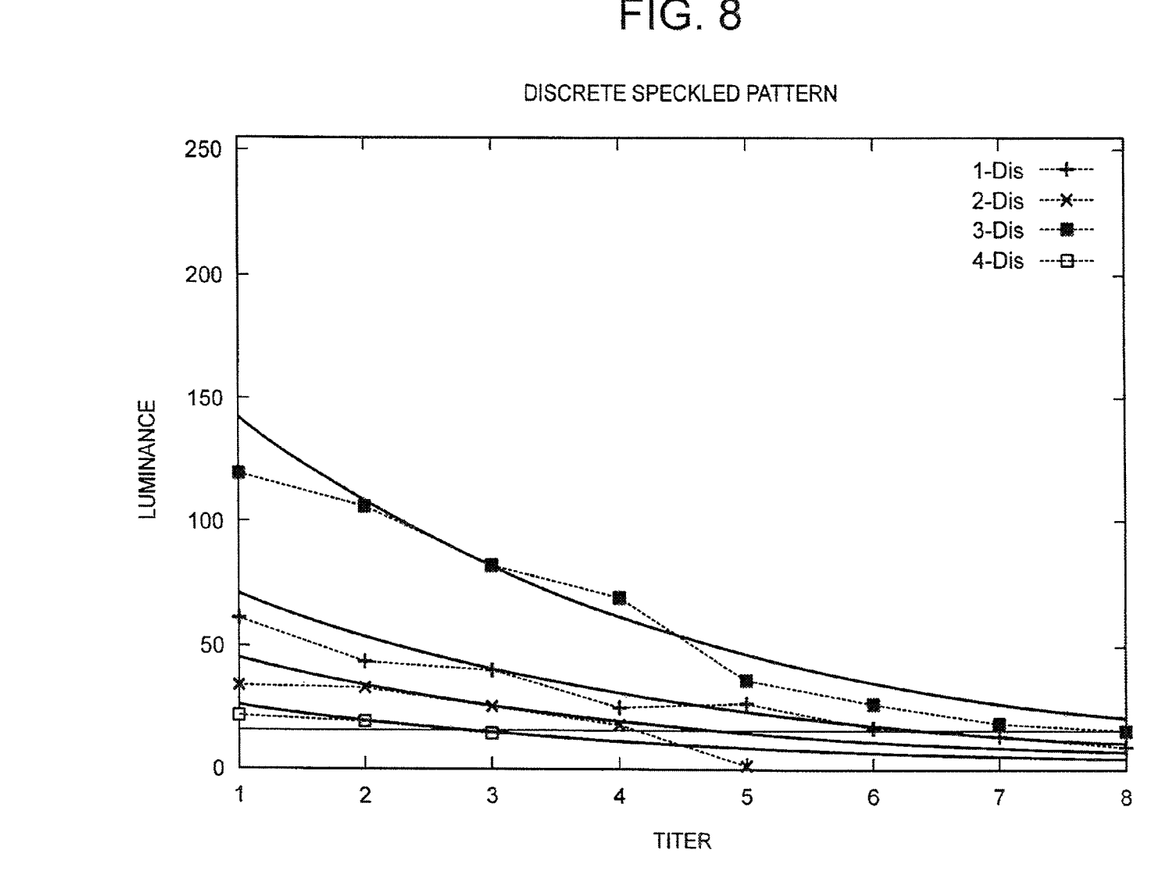
FIG. 8 is an explanatory diagram depicting the relationship between the titer and the luminance in discrete speckled pattern.

FIGS. 5 to 8 are each an explanatory diagram depicting the relationship between the titer prediction curve calculated for the corresponding staining pattern and the measurement value calculated from the obtained image. In detail, the graph depicted in FIG. 5 represents the relationship between the titer and the luminance in speckled pattern, the graph depicted in FIG. 6 represents the relationship between the titer and the luminance in homogeneous pattern, the graph depicted in FIG. 7 represents the relationship between the titer and the luminance in nucleolar pattern, and the graph depicted in FIG. 8 represents the relationship between the tier and the luminance in discrete speckled pattern.

In each of the graphs depicted in FIGS. 5 to 8, the points of cross mark, x mark, solid square mark, and hollow square mark represent the luminance values at each titer calculated from the images of the cases of the corresponding staining pattern, and the solid curves represent the calculated titer prediction curves. In each graph, the straight line between luminance 0 and 50 in parallel with the horizontal axis is the threshold for the corresponding staining pattern.

Since the measurement value at the titer of 160-fold is used in the estimation of each titer prediction curve, the luminance of the titer prediction curve and the calculated measurement value match at the titer of 160-fold, as depicted in FIGS. 5 to 8. Moreover, in FIGS. 5 to 8, the calculated titer prediction curve approaches the measurement value at each titer. In particular, the measurement value gradually approaches the titer prediction curve as the titer increases.

For instance, in the example depicted in FIG. 5, both the measurement value of case 1 and the luminance of the titer prediction curve are below the threshold at the titer of 5120-fold. Hence, the titer of case 1 is determined as 2560-fold both in the case of using the titer prediction curve and in the case of using the measurement value. The measurement value of each of cases 3 and 4 is below the threshold at the titer of 2560-fold. Hence, the titer of each of cases 3 and 4 is determined as 1280-fold both in the case of using the titer prediction curve and in the case of using the measurement value.

On the other hand, the measurement value of case 2 was collected only up to the titer of 320-fold, from which the titer cannot be determined. The use of the titer prediction curve according to the present invention, however, reveals that the luminance is below the threshold at the titer of 640-fold. The titer of case 2 can thus be determined as 320-fold through the use of the titer prediction curve.

Even in the case where the staining pattern is different as in FIGS. 6 to 8, the titer can be determined in the same way as the staining pattern depicted in FIG. 5.

Note that, in the range where the luminance indicated by the titer prediction curve is high, the luminance adjusting function of the microscope acts to distort the luminance of the measurement value due to excessively high luminance, as a result of which a gap between the luminance indicated by the measurement value and the luminance indicated by the titer prediction curve is observed (for example, cases 1, 3, and 4 at the titer of 40-fold in FIG. 5).

Figure 9:
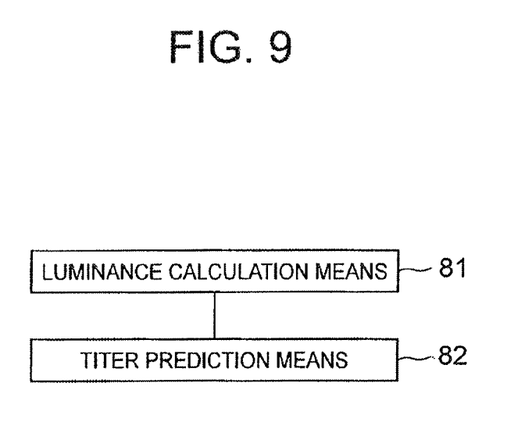
FIG. 9 is a block diagram schematically depicting an antinuclear antibody image analysis system according to the present invention.

The following describes an overview of the present invention. FIG. 9 is a block diagram schematically depicting an antinuclear antibody image analysis system according to the present invention. The antinuclear antibody image analysis system according to the present invention includes: luminance calculation means 81 (e.g. the luminance calculation means 14) which calculates luminance of a cell nucleus extracted from an antinuclear antibody image of a designated dilution ratio; and titer prediction means 82 (e.g. the titer prediction means 15) which predicts an antinuclear antibody titer, using a staining pattern specified from a staining form of the cell nucleus and the luminance at at least one dilution ratio.

Such a structure reduces the operating cost in predicting the titer using the antinuclear antibody image.

The titer prediction means 82 may predict the antinuclear antibody titer by calculating, based on the specified staining pattern and the calculated luminance at a specific dilution ratio, a titer prediction curve (e.g. the curve expressed by Formula 2 or 3) representing a relationship between each dilution ratio and luminance, and specifying, from the titer prediction curve, a dilution ratio at which luminance is below a threshold preset depending on the staining pattern.

The luminance at each titer can be complemented by calculating the titer prediction curve, with there being no need to prepare the antinuclear antibody at a plurality of dilution ratios. This reduces the operating cost in titer prediction.

The titer prediction means 82 may predict, as the antinuclear antibody titer, a maximum dilution ratio from among all dilution ratios that are lower than the specified dilution ratio and are used to determine the titer.

The luminance calculation means 81 may calculate an average value of a predetermined color (e.g. green in RGB) from each cell nucleus, and set, as the luminance, an average value of the color of the whole image calculated using the calculated average value of each cell nucleus.

The titer prediction means 82 may predict the antinuclear antibody titer for each of one or more staining patterns specified from one antinuclear antibody image. By predicting the titers of a plurality of possible staining patterns from one antinuclear antibody image in this way, the operating cost in titer prediction can be further reduced.

Although the present invention has been described with reference to the foregoing exemplary embodiments and examples, the present invention is not limited to the foregoing exemplary embodiments and examples. Various changes understandable by those skilled in the art can be made to the structures and details of the present invention within the scope of the present invention.

This application claims priority based on Japanese Patent Application No. 2013-255558 filed on Dec. 11, 2013, the disclosure of which is incorporated herein in its entirety.

INDUSTRIAL APPLICABILITY

The present invention is suitable for use in, for example, a system for analyzing stained samples of antinuclear antibodies according to the immunofluorescence through image data and evaluating fluorescence patterns and antibody titers.

REFERENCE SIGNS LIST 11 image input means
12 cell nucleus extraction means
13 staining pattern determination means
14 luminance calculation means
15 titer prediction means
16 prediction result output means

The invention claimed is:

1. An antinuclear antibody image analysis system comprising:
   a hardware including a processor
   a luminance calculation unit, implemented at least by the hardware, which calculates luminance of a cell nucleus extracted from an antinuclear antibody image of a designated dilution ratio; and
   a titer prediction unit, implemented at least by the hardware, which predicts an antinuclear antibody titer, using a staining pattern specified from a staining form of the cell nucleus and the luminance at at least one dilution ratio, and
   wherein the titer prediction unit predicts the antinuclear antibody titer for each of one or more staining patterns specified from one antinuclear antibody image.

2. The antinuclear antibody image analysis system according to claim 1, wherein the titer prediction unit predicts the antinuclear antibody titer by calculating, based on the specified staining pattern and the calculated luminance at a specific dilution ratio, a titer prediction curve representing a relationship between each dilution ratio and luminance, and specifying, from the titer prediction curve, a dilution ratio at which luminance is below a threshold preset depending on the staining pattern.

3. The antinuclear antibody image analysis system according to claim 2, wherein the titer prediction unit predicts, as the antinuclear antibody titer, a maximum dilution ratio from among all dilution ratios that are lower than the specified dilution ratio and are used to determine the titer.

4. The antinuclear antibody image analysis system according to claim 1, wherein the luminance calculation unit calculates an average value of a predetermined color from each cell nucleus, and sets, as the luminance, an average value of the color of the whole image calculated using the calculated average value of each cell nucleus.

5. An antinuclear antibody image analysis method comprising:
   calculating luminance of a cell nucleus extracted from an antinuclear antibody image of a designated dilution ratio;
   predicting an antinuclear antibody titer, using a staining pattern specified from a staining form of the cell nucleus and the luminance at at least one dilution ratio; and
   predicting the antinuclear antibody titer for each of one or more staining patterns specified from one antinuclear antibody image.

6. The antinuclear antibody image analysis method according to claim 5, wherein the antinuclear antibody titer is predicted by calculating, based on the specified staining pattern and the calculated luminance at a specific dilution ratio, a titer prediction curve representing a relationship between each dilution ratio and luminance, and specifying, from the titer prediction curve, a dilution ratio at which luminance is below a threshold preset depending on the staining pattern.

7. A non-transitory computer readable information recording medium storing an antinuclear antibody image analysis program, when executed by a processor, that performs a method for:
   calculating luminance of a cell nucleus extracted from an antinuclear antibody image of a designated dilution ratio;
   predicting an antinuclear antibody titer, using a staining pattern specified from a staining form of the cell nucleus and the luminance at at least one dilution ratio; and
   predicting the antinuclear antibody titer for each of one or more staining patterns specified from one antinuclear antibody image.

8. The non-transitory computer readable information recording medium according to claim 7, the antinuclear antibody titer is predicted by calculating, based on the specified staining pattern and the calculated luminance at a specific dilution ratio, a titer prediction curve representing a relationship between each dilution ratio and luminance, and specifying, from the titer prediction curve, a dilution ratio at which luminance is below a threshold preset depending on the staining pattern.

* * * * *